(12) United States Patent
Bertola et al.

(10) Patent No.: US 6,392,088 B1
(45) Date of Patent: May 21, 2002

(54) PROCESS FOR THE PRODUCTION OF DIMETHYLESTERS OF UNSATURATED DICARBOXYLIC ANHYDRIDES

(75) Inventors: Aldo Bertola, Milan (IT); Myriam Hobe, Bas-Oha (BE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/446,394

(22) PCT Filed: Dec. 2, 1997

(86) PCT No.: PCT/EP97/06738

§ 371 Date: Jan. 21, 2000

§ 102(e) Date: Jan. 21, 2000

(87) PCT Pub. No.: WO98/58897

PCT Pub. Date: Dec. 30, 1998

(30) Foreign Application Priority Data

Jun. 24, 1997 (BE) .............................................. 9700535

(51) Int. Cl.[7] .......................... C07C 69/52; C07C 69/34
(52) U.S. Cl. ...................... 560/205; 560/190; 560/205; 560/218
(58) Field of Search ................................ 560/190, 203, 560/204

(56) References Cited

U.S. PATENT DOCUMENTS

| | | | | |
|---|---|---|---|---|
| 4,331,812 A | * | 5/1982 | Smiley | 560/191.19 |
| 5,231,222 A | * | 7/1993 | Papa et al. | 560/265.205 |
| 5,536,856 A | * | 7/1996 | Harrison et al. | 554/164 |

FOREIGN PATENT DOCUMENTS

| | | | |
|---|---|---|---|
| DE | 42-41448 A1 | * | 6/1994 |
| DE | 4241448 | | 6/1994 |
| DE | 196105-64 | * | 9/1997 |
| DE | 19610564 | | 9/1997 |
| EP | 00-09886 | * | 4/1980 |
| EP | 0009886 | | 4/1980 |
| EP | 0158499 | | 10/1985 |
| EP | 01-58499 | * | 10/1985 |
| EP | 0521488 | | 1/1993 |
| EP | 05-21488 | * | 1/1993 |
| GB | 1173089 | | 12/1969 |
| GB | 11-73089 | * | 12/1969 |
| GB | 12-62645 | * | 2/1972 |
| GB | 1262645 | | 2/1972 |
| WO | 8800937 | | 2/1988 |
| WO | 88-00937 | * | 2/1988 |

* cited by examiner

*Primary Examiner*—Gary Geist
*Assistant Examiner*—Z. Tucker
(74) *Attorney, Agent, or Firm*—Stevens, Davis, Miller & Mosher, LLP

(57) ABSTRACT

An improved process for the production of high quality unsaturated dimethylesters by reacting dicarboxylic anhydrides, typically maleic anhydride or phthalic anhydride, with methanol. The process is characterized by the fact that the esterification is performed in two steps, the step 1 consisting in a non catalytic reaction of formation of monomethylesters, and the step 2 consisting in the catalytic reaction of formation of dimethylesters from the monomethylester, the said catalytic reaction taking place in a reactor consisting of a multi-tray column where the liquid phase containing the mono and diester mixture flows downwards from each tray coming to contact with a progressively drier upflowing stream of vapors in countercurrent, which continuously removes the water formed in the reaction from the liquid phase. The process uses an alkylbenzene sulfonic acid with an alkyl radical containing from 10 to 13 carbon atoms as esterification catalyst.

20 Claims, 1 Drawing Sheet

Figure 1:
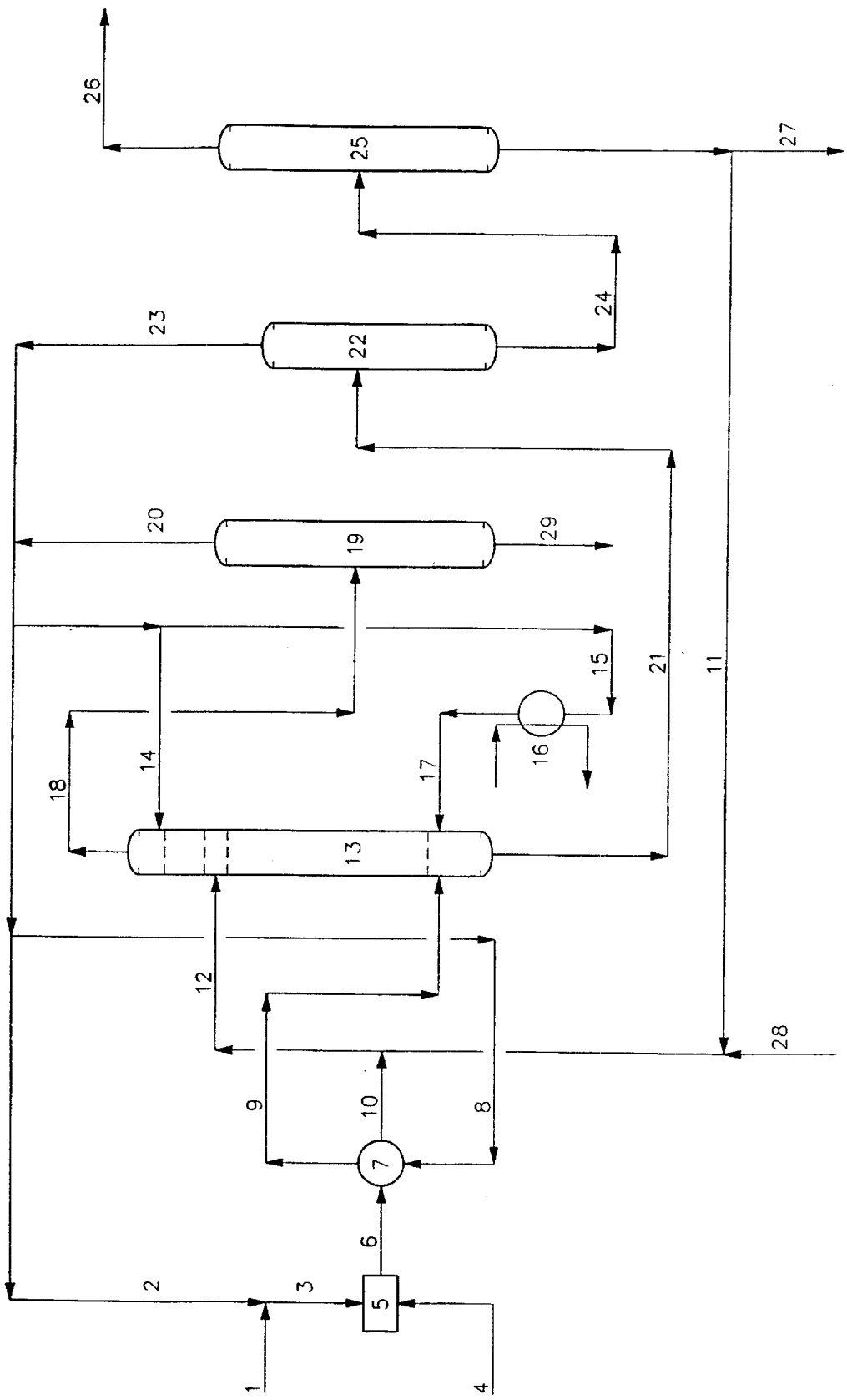

PROCESS FOR THE PRODUCTION OF DIMETHYLESTERS OF UNSATURATED DICARBOXYLIC ANHYDRIDES

The present invention relates to an improved process for the production of esters by reacting dicarboxylic acids or anhydrides (typically maleic anhydride or phthalic anhydride) with methanol, in the presence of a catalyst consisting of an alkyl benzene sulfonic acid with an alkyl radical containing from 8 to 16 carbon atoms, preferably from 10 to 13 carbon atoms.

The production of dimethyl maleate (DMM) from maleic anhydride (MAN) and methanol has received special attention and interest due to the increasing use of DMM as feedstock for the production of derivatives such as gamma butyrolactone (GBL), tetrahydrofuran (THF) and butanediol (BDO).

Various methods for production of DMM have been described in the literature.

The esterification of MAN proceeds stepwise via a monoesterification reaction, with production of monomethyl maleate (MMM), and an esterification reaction with production of DMM, according to the following equations:

Monoesterification

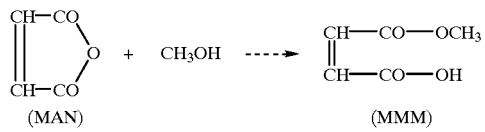

(MAN)                                      (MMM)

Esterifications

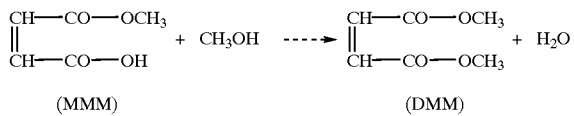

(MMM)                                      (DMM)

Other esterifications, like the production of dimethylphthalate from phthalic anhydride and methanol, proceed in the same way.

These reactions are normally carried out in two separate reactors.

The monoesterification reaction is normally effected non catalytically, while the esterification reaction is carried out in the presence of a catalyst in order to accelerate the reaction.

Because the esterification is an equilibrium reaction, various methods have been described in the literature in which the equilibrium is displaced by removal of water in order to allow a high yield, high conversion rate production of the ester.

In the esterifications, the most widely used catalysts are strong homogeneous acid compounds, such as sulfuric acid or sulfonic acids (typically p-toluene sulfonic acid) as suggested in British Patents 1,173,089 and 1,262,645.

Other patents, such as European Patent Publications 009, 886 and 158,499 suggest the use of alkyl sulfonic acids having formula RSO3H.

The above catalysts, however, present several disadvantages in the preparation of an ester like DMM, which must meet critical purity specifications.

In fact, in order to recover the DMM produced, the catalyst must be removed.

Neutralisation with alkali, followed by washing with water, is a standard method employed by the esterification industry for the above removal.

The neutralisation and washing steps, however, produce significant quantities of waste water, where besides the catalyst, salts of acid compounds such as maleic anhydride or MMM in traces are present, as well as DMM which is somewhat soluble in water, resulting in a loss of process efficiency and major environmental problems.

Moreover, since the acid catalyst is destroyed in the neutralisation, its consumption penalizes production costs.

According to the present invention, to avoid the problems that arise from the neutralisation it has been thought to vaporize and distill the ester product by separating it from a residue containing the acid catalyst which is bound to be recycled to the esterification, as an integral part of the process object of the invention However, such procedure results non-satisfactory in case standard acid catalysts are employed in the esterification.

In fact, the aforementioned catalysts tend to form sulfonate esters which derive from the esterification of the acid catalyst obtained by reacting it with the alcohol reagent.

No matter whether the sulfonic esters are distilled with DMM or are subject to thermal decomposition, they release sulfur compounds which contaminate the ester product.

In case the DMM produced is used as a feed for the production of GBL, THF and BDO, sulfur impurities shall be absent, or limited to a fraction of a part per million (say 0.5 ppm. or less).

In fact, the presence of sulfur in DMM would result in rapid poisoning of the hydrogenation catalyst employed in the conversion of DMM into GEL, THF and BDO.

Furthermore, because of the formation of sulfonic esters and their contamination either with metals resulting from corrosion or with heavy organic by-products, the standard acid catalysts have shown to rapidly lose their activity and as a result of that to be only partly reusable if an ester vaporization and distillation process is employed.

To avoid the disadvantages associated with the use of standard homogeneous acid catalysts, various methods have been described.

In WO 88/00937 DAVY McKEE described the production of esters of maleic anhydride, preferably diethylmaleate, using a solid ion exchange resin containing SO3H groups.

Although feasible, the use of a heterogeneous catalyst complicates the process because of the complex design the multistage esterification system is based on, and in principle it cannot grant a completely sulfur free product. This ought to be ascribed to the tendency the resins have to lose part of their active sulfonic groups at the start and in the course of the operation, with the associated gradual decrease in their catalytic activity.

To completely overcome the abovementioned drawbacks and complications, the present invention provides a process for producing esters from a dicarboxylic acid or anhydride that react with methanol in the presence of a homogeneous type catalyst, characterized by the fact that the amount of sulfur in the product meets the specifications required by the further processing of the abovementioned ester product consisting of hydrogenations and also by the fact that the catalyst can be recovered and reused in the process causing no major enviromental problems.

The abovementioned results are obtained by using an alkylbenzene sulfonic acid having an alkyl radical containing from 8 to 16 carbon atoms, preferably from 10 to 13 carbon atoms (i.e. : n-decylbenzene sulfonic acid, n-undecylbenzene sulfonic acid, n-dodecylbenzene sulfonic acid, n-tridecylbenzene sulfonic acid)as esterification catalyst.

Mixtures of alkylbenzene sulfonic acids containing alkyl chains formed by between 8 and 16 carbon atoms are also adequate.

Similar esterification catalysts have been suggested by UNION CARBIDE in E.P. 0521 488 A2.

However, it can be noted that the above mentioned patent owned by UNION CARBIDE concerns the esterification of monocarboxylic acids having from 1 to 4 carbon atoms (acetic acid, propionic acid, butyric acid and alikes) with alcohols having from 2 to 8 carbon atoms.

Furthermore the process described by UNION CARBIDE concerns the production of esters which vaporize together with water in the esterification.

Instead, the process object of the present invention applies to dicarboxylic acids or anhydrides esterified with an alcohol only containing one carbon atom (i.e. methanol). The product of the esterification-DMM, dimethylphthalate and alikes-does not vaporize during the process.

Furthermore, in the process object of the present invention the esterification is performed in a reactor consisting of a multi-tray column where the liquid phase containing the mono and diester mixture flows downwards from each tray coming to contact with a progressively drier upflowing stream of vapors in countercurrent, which remove the water formed in the reaction from the liquid phase.

The esterification reaction is carried out at operating conditions (i.e. number of trays, retention time, operating pressure and temperature) which are selected so as to cause all of the MAN and MMM to be converted into DMM with high selectivity.

DESCRIPTION OF THE PROCESS

The preferred embodiments of the process object of the present invention can be illustrated with reference to the attached flow diagram of FIG. 1, which shows a procedure for putting this invention in practice for the production of DMM from MAN and methanol.

Fresh methanol (line 1) is mixed with recycle methanol (line 2) to form a methanol stream (line 3) that feeds the process.

Molten MAN (line 4) joins the methanol stream in monoesterification reactor 5, where MAN is to a large extent converted into MMM.

The operating conditions at the monoesterification reactor 5 are:

| Pressure: | | from 0.1 to 5 bar |
|---|---|---|
| | preferably | from 2 to 4 bar |
| Temperature: | | from 20 to 160° C. |
| | preferably | from 100 to 130° C. |
| Methanol: MAN molar ratio: | | from 1.1:1 to 5:1 |
| | preferably | from 1.5:1 to 3:1 |
| Retention time: | | from 5 to 60 min. |
| | preferably | from 10 to 30 min. |

The effluent from monoesterification reactor 5 (line 6) is cooled in exchanger 7 where it vapourises a liquid methanol stream (line 8).

Methanol vapours from exchanger 7 (line 9) are fed to the bottom of esterification column 13 for heat recovery purposes.

The cooled monoester stream from exchanger 7 (line 10), is mixed with a DMM recycle stream containing the acid esterification catalyst (line 11) and the resulting mixture (line 12) flows to esterification column 13.

N-dodecyl benzene sulfonic acid (DBSA) is used as a catalyst.

In column 13 the esterification is completed by a further MMM reaction of with methanol and production of DMM.

There are some trays in the section above the feed inlet (line 12) of esterification column 13 for washing out and recovering by means of liquid methanol (line 14) any MAN, MMM or DMM present in the vapours leaving the esterification section of the column itself.

The operating conditions in the esterification section of column 13 are:

| Pressure: | | from 0.1 to 5 bar |
|---|---|---|
| | preferably | from 0.1 to 1 bar |
| Temperature: | | from 80 to 150° C. |
| | preferably | from 90 to 130° C. |
| Retention time: | | from 1 to 5 hr. |
| | preferably | from 1.5 to 3 hr. |
| DBSA concentration (as SO3H): | | from 0.1 to 2.0% wt. |
| | preferably | from 0.3 to 0.8% wt. |

In the esterification column the liquid stream passes downwards from each tray to the next lower tray against an upflowing stream of methanol and water vapours produced in the esterification.

Flowing downwards, the unreacted acid or anhydride fractions come in contact with progressively drier methanol vapours. By providing an adequate number of trays with appropriate retention times, at the bottom of esterification column 13 it is possible to produce DMM with some methanol in it, but with a very low MMM and water content.

The heat needed to vaporize and remove the water present in the reaction and the excess methanol is supplied by vaporizing a methanol stream (line 15) in heater 16 and feeding the methanol vapours (lime 17) at the bottom end of esterification colunm 13.

After leaving esterification column 13 (line 18) the vapours flow to column 19 where dry methanol is separated at the top (line 20) to be reused in the process, while reaction water is collected at the bottom of column 19 to be disposed of (line 29).

When the crude ester produced leaves the esterification column (line 21) besides DMM it contains methanol and DBSA catalyst, with only little amounts of free acids and water.

This stream is first processed in stripper 22 where excess methanol is recovered and recycled (line 23).

The crude ester that leaves stripper 22 (line 24) is eventually processed in column 25 that operates under vacuum.

Column 25 separates the DMM product at the top from the bottom stream that contains DMM and any non-converted MMM and DBSA catalyst (line 26). This is recycled to esterification column 13.

A small fraction of recycle stream 11 is intermittently purged out (line 27) for control of by-product accumulation.

Freshly made DBSA catalyst (line 28) is intermittently added to compensate for the negligible losses of catalyst that occur in the process.

The DMM produced in the process object of the present invention meets very high purity standards and is fully adequate to be converted into derivatives such as GBL, THF and BDO by selective hydrogenation.

The sulfur content of the DMM will be less than 500 ppb.

What is claimed is:

1. A process for the production of high quality unsaturated dimethylesters by reacting unsaturated dicarboxylic anhydrides with methanol in a two step process comprising:

(1) reacting in step 1 the unsaturated dicarboxylic anhydrides with a molar excess of methanol in a non-catalytic reaction to form the corresponding monomethylesters; and (2) reacting in step 2 the resulting monomethylesters, and methanol in a catalytic reaction in presence of an alkylbenzene sulfonic acid, having an alkyl radical containing 8 to 16 carbon atoms, to form the corresponding dimethylesters, wherein the catalytic reaction of step 2 is performed in a multi-tray column where the liquid phase containing the mono-and dimethylester mixture flows downwards from each tray coming to contact with a progressively drier upflowing stream of methanol vapours in countercurrent flow.

2. A process as claimed in claim 1, wherein said process comprises:

(a) continuously supplying in step 1 the unsaturated dicarboxylic anhydride feed and the molar excess of methanol to a non-catalytic monoesterification reactor to form the corresponding monomethylester, (b) continuously supplying in step 2 the resulting monomethylester of step 1 mixed with a recycling stream containing the alkylbenzene sulfonic acid in dimethylester and continuously supplying a molar excess of methanol to the multi-tray column, (c) maintaining said multi-tray column during step 2 at a temperature which is adequate to form and maintain a methanol vapour stream injected at the bottom of the multi-tray column, (d) recovering from said multi-tray column a vapour effluent containing, in addition to methanol, the water produced in the reaction of step 2, (e) recovering from said multi-tray column a liquid product containing crude dimethylester product, some methanol and the alkylbenzene sulfonic acid, (f) recovering the methanol contained in the crude dimethylester product by stripping, (g) distilling the stripped crude dimethylester product to recover pure dimethylester as an overhead stream and separate a dimethylester rich stream containing the alkylbenzene sulfonic acid as a bottom stream, (h) recycling the dimethylester rich stream containing the alkylbenzene sulfonic acid to the multi-tray column.

3. A process as claimed in claim 1, wherein the unsaturated dicarboxylic anhydride is maleic anhydride or phthalic anhydride.

4. A process as claimed in claim 2, wherein the unsaturated dicarboxylic anhydride is maleic anhydride or phthalic anhydride.

5. A process as claimed in claim 1, wherein the alkylbenzene sulfonic acid has an alkyl radical containing 10 to 13 carbon atoms, is used.

6. A process as claimed in claim 2, wherein an alkylbenzene sulfonic acid, having an alkyl radical containing 10 to 13 carbon atoms, is used.

7. A process as claimed in claim 1, wherein n-dodecylbenzene sulfonic acid is used as alkylbenzene sulfonic acid.

8. A process as claimed in claim 2, wherein n-dodecylbenzene sulfonic acid is used as alkylbenzene sulfonic acid.

9. A process as claimed in claim 1, wherein the concentration of the alkylbenzene sulfonic acid (as-SO3H) ranges from 0.1 to 2.0% by weight.

10. A process as claimed in claim 2, wherein the concentration of the alkylbenzene sulfonic acid (as-SO3H) ranges from 0.1 to 2.0% by weight.

11. A process as claimed in claim 1, wherein the non-catalytic reaction of step 1 is performed at a temperature of 20 to 160° C. and at a pressure of 0.1 to 5 bars.

12. A process as claimed in claim 2, wherein the non-catalytic reaction of step 1 is performed at a temperature of 20 to 160° C. and at a pressure of 0.1 to 5 bars.

13. A process as claimed in claim 1, wherein the methanol unsaturated dicarboxylic anhydride molar ratio in the non-catalytic reaction of step 1 ranges from 1.1:1 to 5:1.

14. A process as claimed in claim 2, wherein the methanol unsaturated dicarboxylic anhydride molar ratio in the non-catalytic reaction of step 1 ranges from 1.1:1 to 5:1.

15. A process as claimed in claim 1, wherein the retention time in the non-catalytic reaction of step 1 ranges from 5 to 60 minutes.

16. A process as claimed in claim 2, wherein the retention time in the non-catalytic reaction of step 1 ranges from 5 to 60 minutes.

17. A process as claimed in claim 1, wherein the catalytic reaction of step 2 is performed at a temperature of 80 to 150° C. and at a pressure of 0.1 to 5 bars.

18. A process as claimed in claim 2, wherein the catalytic reaction of step 2 is performed at a temperature of 80 to 150° C. and at a pressure of 0.1 to 5 bars.

19. A process as claimed in claim 1, wherein the retention time in the catalytic reaction of step 2 ranges from 1 to 5 hours.

20. A process as claimed in claim 2, wherein the retention time in the catalytic reaction of step 2 ranges from 1 to 5 hours.

* * * * *